United States Patent
Rittsteiger et al.

(10) Patent No.: US 10,392,340 B2
(45) Date of Patent: Aug. 27, 2019

(54) PURIFICATION OF CRUDE ISOPHORONEDIAMINE BY PARTIAL CONDENSATION IN SERIES WITH TOTAL CONDENSATION

(71) Applicant: Evonik Degussa GmbH, Essen (DE)

(72) Inventors: Anne Rittsteiger, Olfen (DE); Jan Caßens, Recklinghausen (DE); Axel Hengstermann, Senden (DE); Cord Knoop, Haltern am See (DE); Anja Müller, Dortmund (DE); Alexander Martin Rüfer, Recklinghausen (DE)

(73) Assignee: Evonik Degussa GmbH, Essen (DE)

( * ) Notice: Subject to any disclaimer, the term of this patent is extended or adjusted under 35 U.S.C. 154(b) by 265 days.

(21) Appl. No.: 15/642,382

(22) Filed: Jul. 6, 2017

(65) Prior Publication Data
US 2018/0029971 A1    Feb. 1, 2018

(30) Foreign Application Priority Data

Jul. 27, 2016 (EP) ..................... 16181360

(51) Int. Cl.
*C07C 209/84* (2006.01)
*B01D 3/10* (2006.01)
*B01D 3/14* (2006.01)

(52) U.S. Cl.
CPC .............. *C07C 209/84* (2013.01); *B01D 3/10* (2013.01); *B01D 3/143* (2013.01); *C07C 2601/14* (2017.05)

(58) Field of Classification Search
None
See application file for complete search history.

(56) References Cited

U.S. PATENT DOCUMENTS

| | | | |
|---|---|---|---|
| 3,352,913 | A | 11/1967 | Schmitt et al. |
| 7,256,313 | B2 | 8/2007 | Funke et al. |

(Continued)

FOREIGN PATENT DOCUMENTS

| | | |
|---|---|---|
| CN | 104230721 A | 12/2014 |
| EP | 1529027 A1 | 5/2005 |

(Continued)

OTHER PUBLICATIONS

Luyben, W., Alternative Control Stuctures for Distillation Columns with Partial Condensers, Ind. Eng. Chem. Res., 2004, vol. 43 pp. 6416-6429. (Year: 2004).*

(Continued)

*Primary Examiner* — Renee Robinson
*Assistant Examiner* — Derek N Mueller
(74) *Attorney, Agent, or Firm* — Philip P. McCann; Nexsen Pruet PLLC

(57) ABSTRACT

The present invention is directed to a process for fine purification of isophoronediamine from the production of isophoronediamine wherein the crude isophoronediamine I is subjected to a fine purification by means of two vacuum distillation columns, wherein I. in the first vacuum distillation column K I low-boiling by-products still present are removed, and a crude IPDA II is transferred from the bottom of K I into the vacuum distillation column K II, II. and in the second vacuum distillation column K II the isophoronediamine is obtained in pure form overhead and separated from the organic residues, wherein the first condenser is a partial condenser and the pure IPDA is removed therein, and wherein the second condenser is a total condenser and the residual portion of the vapor stream from K II is completely condensed therein and recycled as return stream into the first vacuum distillation column K I.

20 Claims, 2 Drawing Sheets

(56) References Cited

U.S. PATENT DOCUMENTS

| | | |
|---|---|---|
| 7,497,931 B2 | 3/2009 | Funke et al. |
| 8,198,481 B2 | 6/2012 | Kuppinger et al. |
| 8,252,120 B2 | 8/2012 | Nordhoff et al. |
| 8,293,941 B2 | 10/2012 | Kuppinger et al. |
| 8,362,299 B2 | 1/2013 | Hengstermann et al. |
| 8,481,784 B2 | 7/2013 | Kuppinger et al. |
| 8,877,976 B2 | 11/2014 | Lettmann et al. |
| 8,895,683 B2 | 11/2014 | Kuppinger et al. |
| 2017/0298003 A1* | 10/2017 | Rittsteiger ............ B01D 3/143 |

FOREIGN PATENT DOCUMENTS

| | | |
|---|---|---|
| EP | 1529028 A2 | 5/2005 |
| EP | 2649042 A1 | 10/2013 |
| WO | 2004020386 A1 | 3/2004 |
| WO | 2004024668 A2 | 3/2004 |
| WO | 2012076315 A1 | 6/2012 |
| WO | 2012126869 A1 | 9/2012 |
| WO | 2015038679 A1 | 3/2015 |

OTHER PUBLICATIONS

Kohlstruk et al, U.S. Appl. No. 15/541,733, filed Jul. 6, 2017.
Langkabel et al, U.S. Appl. No. 15/602,723, filed May 23, 2017.
Langkabel et al, U.S. Appl. No. 15/603,966, filed May 24, 2017.
Langkabel et al, U.S. Appl. No. 15/604,118, filed May 24, 2017.
Rittsteiger et al, U.S. Appl. No. 15/473,892, filed Mar. 30, 2017.
Rüfer et al, U.S. Appl. No. 15/604,873, filed May 25, 2017.
Rüfer et al, U.S. Appl. No. 15/604,988, filed May 25, 2017.
Rüfer et al, U.S. Appl. No. 15/605,268, filed May 25, 2017.

* cited by examiner

PURIFICATION OF CRUDE ISOPHORONEDIAMINE BY PARTIAL CONDENSATION IN SERIES WITH TOTAL CONDENSATION

This application claims the benefit of European Application No. 16181360.5 filed on Jul. 27, 2016, the disclosure of which is expressly incorporated herein by reference.

BACKGROUND

The invention relates to the fine purification of isophoronediamine (IPDA) using a two-stage column setup comprising a partial condenser and recycling.

The production of IPDA by aminating hydrogenation of isophorone nitrile (IPN) is known and has already been described numerous times.

In the simplest case (U.S. Pat. No. 3,352,913), IPN is reacted in the presence of hydrogen and of an excess of ammonia over a cobalt catalyst. IPN and ammonia initially react with elimination of water to form isophorone nitrile imine, IPNI, which is subsequently hydrogenated to IPDA:

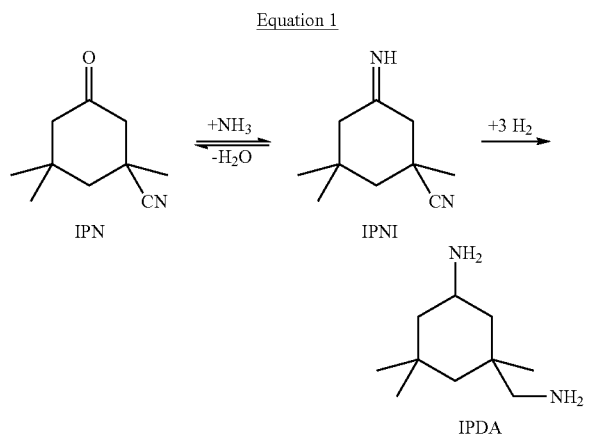

Equation 1

In addition, processes for producing isophoronediamine are known from CN 104230721A, EP 2 649 042A and WO 2012126869A.

In EP 2 649 042A isophoronediamine is produced from isophorone nitrile in a one- or two-stage reaction. Isophorone nitrile is initially iminated with ammonia to afford isophorone nitrile imine. Said isophorone nitrile imine is hydrogenated to afford isophoronediamine in the second step. The purification that follows the reaction is likewise divided into two steps. The low boilers are initially removed in a plurality of distillation columns, said low boilers including hydrogen, inert gases, ammonia and low-boiling impurities (low boiler removal). In a final step the pure isophoronediamine is then obtained via two vacuum distillation columns. The first column in turn serves to remove any remaining relatively low-boiling by-products. In the second column the isophoronediamine is obtained in pure form overhead and thus separated from the organic residues (high boilers).

WO 2015/038679 describes a process for separating ammonia and a diamine. The distillation is effected here by means of a sequence of three distillation columns, wherein ammonia is removed as low boiler overhead in each column.

The two applications EP 1529027 and EP 1529028 describe the fine purification of IPDA by distillation in a setup composed of at least two columns. In this case, there is both removal of low- and high-boiling secondary components and separation into two separate IPDA fractions. These each differ in terms of their cis/trans ratio.

BRIEF DESCRIPTION OF THE DRAWINGS

The problem addressed by the present invention is that of finding a simple process for fine purification of isophoronediamine with a reduced ammonia content in the pure isophoronediamine.

SUMMARY

It has been found that, surprisingly, through the use of an additional partial condenser at the top of the second column of a two-column system for fine distillation of crude IPDA with recycling of a substream into the first column, it is possible to reduce the ammonia content in the pure IPDA.

DETAILED DESCRIPTION

The invention provides a process for fine purification of isophoronediamine from the production of isophoronediamine by aminating hydrogenation of isophorone nitrile in the presence of at least ammonia, hydrogen, a hydrogenation catalyst and optionally further additions and in the presence or absence of organic solvents to obtain a crude isophoronediamine I, characterized in that the crude isophoronediamine I is subjected to a fine purification by means of two vacuum distillation columns, wherein I. in the first vacuum distillation column K I low-boiling by-products still present are removed, and a crude IPDA II is transferred from the bottom of K I into the vacuum distillation column K II, II. and in the second vacuum distillation column K II the isophoronediamine is obtained in pure form overhead and separated from the organic residues, with two condensers being mounted at the top of the vacuum distillation column K II, wherein the first condenser is a partial condenser and the pure IPDA is removed therein, and wherein the second condenser is a total condenser and the residual portion of the vapor stream from K II is completely condensed therein and recycled as return stream into the first vacuum distillation column K I.

Figure 1:
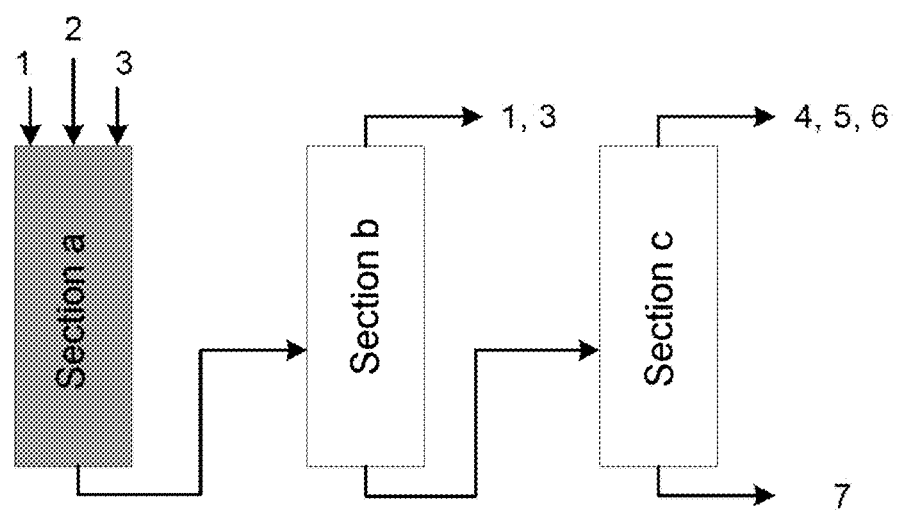

The overall process for producing pure IPDA is divided into three sections (see FIG. 1). In section a the reaction is effected by aminating hydrogenation of isophorone nitrile in a single- or multi-stage process in the presence of at least ammonia, hydrogen and a catalyst. In section b the distillative removal of ammonia and hydrogen to obtain crude IPDA is effected. The distillation may be performed in one or more columns. In section c the fine purification of crude IPDA is effected by distillative removal of IPDA, water, low boilers and high boilers. The fine purification is performed in two vacuum distillation columns.

The crude IPDA I used generally has the following composition in weight % (wt %):
IPDA 75-100 wt %
Water 0-15 wt %
Low boilers 0-6 wt %
High boilers 0-6 wt %
Residual ammonia 10-1000 ppm.

Low boilers are defined as by-products from the process for production of IPDA that have a lower boiling point than IPDA. High boilers are defined as by-products from the process for production of IPDA that have a higher boiling point than IPDA.

The process according to the invention is generally characterized in that the crude isophoronediamine I is subjected to a fine purification by means of two vacuum distillation columns, wherein I. in the first vacuum distillation column K I low-boiling by-products still present are removed, and a crude IPDA II is transferred from the bottom of K I into the vacuum distillation column K II, II. and in the second vacuum distillation column K II the isophoronediamine is obtained in pure form overhead and separated from the organic residues, with two condensers being mounted at the top of the vacuum distillation column K II, wherein the first condenser is a partial condenser and the pure IPDA is removed therein, and wherein the second condenser is a total condenser and the residual portion of the vapor stream from K II is completely condensed therein and recycled as return stream into the first vacuum distillation column K I.

The first vacuum distillation column K I used has the following parameters:
Temperature 40-120° C.
Pressure 10-200 mbar
Theoretical plates 10-80

The composition of the feed stream crude IPDA II from the first vacuum distillation column into the second vacuum distillation column has the following composition:
IPDA 90-100 wt %
High boilers 0-10 wt %
Residual ammonia 10-500 ppm The second vacuum distillation column K II used has the following parameters:
Pressure 10-200 mbar
Tops temperature 80-200° C.
Theoretical plates 5-50

The partial condenser used at the top of the second vacuum distillation column has the following parameters:
Pressure 10-200 mbar
Temperature 80-200° C.

The purity of the pure isophoronediamine is at least 98 wt %. The residual ammonia content in the pure IPDA is less than 50 ppm.

Preferred Procedures and Process Scheme

Figure 2:
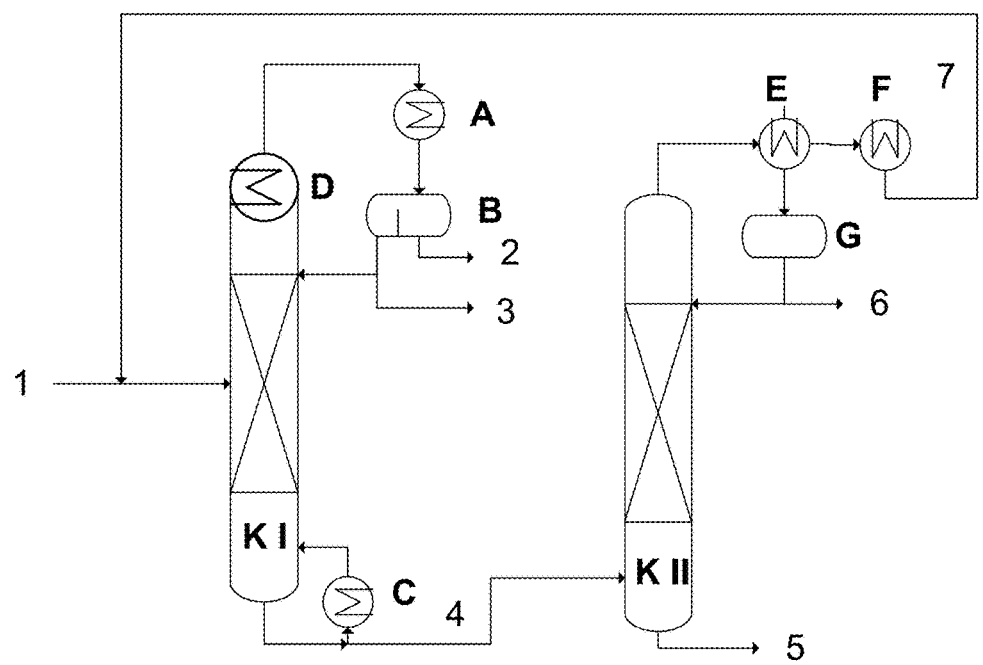

The crude IPDA I is initially passed into the first vacuum distillation column K I; see FIG. 2. The low boilers (stream 2) and water (stream 3) are removed via the top of the first vacuum distillation column. The IPDA leaves the column as bottom stream 4 (crude IPDA II) and is fed to the second vacuum distillation column K II for removal of the high boilers (stream 5) and the recovery of pure IPDA (stream 6). At the top of the second vacuum distillation column there are mounted two series-connected condensers E and F. The first condenser E is operated as a partial condenser. A portion of the vapor stream from the top of the second vacuum distillation column is condensed therein and hence the pure IPDA is obtained as stream 6. The remainder of the vapor stream is completely condensed in the second condenser F and recycled as return stream 7 in the first vacuum distillation column K II. In this way, the majority of the ammonia content from crude IPDA II is also separated from IPDA via the condensers and recycled via stream 7 into the vacuum distillation column K I. This enables the recovery of pure IPDA having a very high quality and very low ammonia content.

EXAMPLES

Example 1

The distillation was simulated using Aspen Plus. For the calculations, a distillation setup consisting of two vacuum distillation columns was considered.

The feed stream used (crude IPDA I) had the following composition in weight % (wt %):
IPDA 85.8 wt %
Water 9.7 wt %
High boilers 2.3 wt %
Low boilers and residual $NH_3$ 2.2 wt %

In the first vacuum distillation column with 42 plates, the organic low boilers and water were separated from the incoming crude IPDA I stream as distillate overhead and, subsequently, the organic and aqueous phases, after condensation, were separated in a decanter. A portion of the organic phase was introduced as return stream into the first vacuum distillation column with a reflux to feed ratio of 1.2. The vacuum distillation column was operated at 110 mbar, a bottom temperature of 178° C. and a top temperature of 114° C.

The feed stream from the first to the second vacuum distillation column had the following composition (crude IPDA II):
IPDA 97.4 wt %
High boilers 2.6 wt %
Residual ammonia 247 ppm.

The second vacuum distillation column having 13 theoretical plates was operated at a bottom temperature of 207° C., a top temperature of 168° C. and a pressure of 110 mbar. The high boilers were removed via the bottom of the vacuum distillation column, and IPDA and the residual ammonia overhead. The top product was guided into a partial condenser as vapor phase and partly condensed at 165° C. and 110 mbar. The mass ratio of partial condensate and uncondensed vapor phase was 130. The uncondensed vapor stream was subsequently fully condensed in a second condenser at 133° C. and 110 mbar and guided as return stream into the first vacuum distillation column.

Pure IPDA having a purity of 99.9 wt % and a residual ammonia content of 15 ppm was obtained from the condensate from the partial condenser.

Through the use of a partial condenser at the top of the second vacuum distillation column, it was thus possible to reduce the residual ammonia content from 247 ppm in the crude IPDA to 15 ppm in the pure IPDA.

Example 2

The distillation was simulated using Aspen Plus. For the calculations, a distillation setup consisting of two vacuum distillation columns was considered.

The feed stream used (crude IPDA I) had the following composition in weight % (wt %):
IPDA 85.8 wt %
Water 9.7 wt %
High boilers 2.3 wt %
Low boilers and residual $NH_3$ 2.2 wt %

In the first vacuum distillation column with 42 plates, the organic low boilers and water were separated from the incoming crude IPDA I stream as distillate overhead and, subsequently, the organic and aqueous phases, after condensation, were separated in a decanter. A portion of the organic phase was introduced as return stream into the first vacuum distillation column with a reflux to feed ratio of 1.2. The vacuum distillation column was operated at 110 mbar, a bottom temperature of 178° C. and a top temperature of 114° C.

The feed stream from the first to the second vacuum distillation column had the following composition (crude IPDA II):
IPDA 97.4 wt %
High boilers 2.6 wt %
Residual ammonia 104 ppm.

The second vacuum distillation column having 13 theoretical plates was operated at a bottom temperature of 207° C., a top temperature of 168° C. and a pressure of 110 mbar. The high boilers were removed via the bottom of the column, and IPDA and the residual ammonia overhead. The top product was guided into a partial condenser as vapor phase and partly condensed at 165° C. and 110 mbar. The mass ratio of partial condensate and uncondensed vapor phase was 344. The uncondensed vapor stream was subsequently fully condensed in a second condenser at 133° C. and 110 mbar and guided as return stream into the first vacuum distillation column.

Pure IPDA having a purity of 99.9 wt % and a residual ammonia content of 15 ppm was obtained from the condensate from the partial condenser.

Through the use of a partial condenser at the top of the second vacuum distillation column, it was possible to reduce the residual ammonia content from 104 ppm in the crude IPDA to 15 ppm in the pure IPDA.

Example 3: Comparative Example

The distillation was simulated using Aspen Plus. For the calculations, the distillation consisting of two vacuum distillation columns was considered. Compared to the inventive examples, in this case, only a total condenser at the top of the second vacuum distillation column was considered. The feed stream used (crude IPDA I) had the following composition in weight % (wt %):
IPDA 85.8 wt %
Water 9.7 wt %
High boilers 2.3 wt %
Low boilers and residual NH$_3$ 2.2 wt %

In the first vacuum distillation column with 42 plates, the organic low boilers and water were separated from the incoming crude IPDA I stream as distillate overhead and, subsequently, the organic and aqueous phases, after condensation, were separated in a decanter. A portion of the organic phase was introduced as return stream into the first vacuum distillation column with a reflux to feed ratio of 1.2. The vacuum distillation column was operated at 110 mbar, a bottom temperature of 178° C. and a top temperature of 114° C.

The feed stream from the first to the second vacuum distillation column had the following composition (crude IPDA II):
IPDA 97.4 wt %
High boilers 2.6 wt %
Residual ammonia 50 ppm.

The second vacuum distillation column having 13 theoretical plates was operated at a bottom temperature of 207° C., a top temperature of 168° C. and a pressure of 110 mbar. The high boilers were removed via the bottom of the column, and IPDA and the residual ammonia overhead. The top product was fully condensed at 133° C.

Pure IPDA having a purity of 99.9 wt % and a residual ammonia content of 50 ppm was obtained from the condensate. It was thus not possible to reduce the residual ammonia content in the pure IPDA compared to the crude IPDA.

It is apparent from the examples adduced that the application of partial condensation clearly leads to a reduction in the residual ammonia content in the pure IPDA. In addition, it was shown that, through the use of the partial condenser downstream of the second vacuum distillation column, even in the case of varying residual ammonia contents in the crude IPDA II stream, the ammonia content in the pure IPDA was well below 50 ppm.

The invention claimed is:

1. A process for fine purification of isophoronediamine from the production of isophoronediamine by aminating hydrogenation of isophorone nitrile in the presence of at least ammonia, hydrogen, a hydrogenation catalyst and optionally further additions and in the presence or absence of organic solvents to obtain a crude isophoronediamine I,
wherein the crude isophoronediamine I is subjected to a fine purification by means of two vacuum distillation columns, wherein
I. in the first vacuum distillation column K I low-boiling by-products still present are removed, and a crude IPDA II is transferred from the bottom of K I into the vacuum distillation column K II,
II. and in the second vacuum distillation column K II the isophoronediamine is obtained in pure form overhead and separated from the organic residues, with two condensers being mounted at the top of the second vacuum distillation column,
wherein the first condenser is a partial condenser and the pure IPDA is removed therein,
and wherein the second condenser is a total condenser and the residual portion of the vapour stream from K II is completely condensed therein and recycled as return stream into the first vacuum distillation column K I.

2. The process according to claim 1, wherein the crude isophoronediamine I has the following composition:
IPDA 75-100 wt %
Water 0-15 wt %
Low boilers 0-6 wt %
High boilers 0-6 wt %
Residual ammonia 10-1000 ppm.

3. The process according to claim 1, wherein the first vacuum distillation column K I has the following parameters:
Temperature 40-120° C.
Pressure 10-200 mbar
Theoretical plates 10-80.

4. The process according to claim 1, wherein the composition of the feed stream crude IPDA II from the first vacuum distillation column into the second vacuum distillation column has the following composition:
IPDA 90-100 wt %
High boilers 0-10 wt %
Residual ammonia 10-500 ppm.

5. The process according to claim 1, wherein the second vacuum distillation column K II has the following parameters:
Pressure 10-200 mbar
Tops temperature 80-200° C.
Theoretical plates 5-50.

6. The process according to claim 1, wherein the partial condenser used at the top of the second vacuum distillation column K II has the following parameters:
Pressure 10-200 mbar
Temperature 80-200° C.

7. The process according to claim 1, wherein the crude isophoronediamine I has the following composition:
IPDA 75-100 wt %
Water 0-15 wt %
Low boilers 0-6 wt %
High boilers 0-6 wt %
Residual ammonia 10-1000 ppm,
and
in that the first vacuum distillation column K I has the following parameters:
Temperature 40-120° C.
Pressure 10-200 mbar
Theoretical plates 10-80
and
in that the composition of the feed stream crude IPDA II from the first vacuum distillation column into the second vacuum distillation column has the following composition:
IPDA 90-100 wt %
High boilers 0-10 wt %
Residual ammonia 10-500 ppm,
and
in that the second vacuum distillation column K II has the following parameters:
Pressure 10-200 mbar
Tops temperature 80-200° C.
Theoretical plates 5-50
and
in that the partial condenser used at the top of the second vacuum distillation column K II has the following parameters:
Pressure 10-200 mbar
Temperature 80-200° C.

8. The process according to claim 1, wherein the purity of the pure isophoronediamine is at least 98% by weight and the residual ammonia content in the pure IPDA is less than 50 ppm.

9. The process according to claim 2, wherein the first vacuum distillation column K I has the following parameters:
Temperature 40-120° C.
Pressure 10-200 mbar
Theoretical plates 10-80.

10. The process according to claim 2, wherein the composition of the feed stream crude IPDA II from the first vacuum distillation column into the second vacuum distillation column has the following composition:
IPDA 90-100 wt %
High boilers 0-10 wt %
Residual ammonia 10-500 ppm.

11. The process according to claim 2, wherein the second vacuum distillation column K II has the following parameters:
Pressure 10-200 mbar
Tops temperature 80-200° C.
Theoretical plates 5-50.

12. The process according to claim 2, wherein the partial condenser used at the top of the second vacuum distillation column K II has the following parameters:
Pressure 10-200 mbar
Temperature 80-200° C.

13. The process according to claim 2, wherein the crude isophoronediamine I has the following composition:
IPDA 75-100 wt %
Water 0-15 wt %
Low boilers 0-6 wt %
High boilers 0-6 wt %
Residual ammonia 10-1000 ppm,
and
in that the first vacuum distillation column K I has the following parameters:
Temperature 40-120° C.
Pressure 10-200 mbar
Theoretical plates 10-80
and
in that the composition of the feed stream crude IPDA II from the first vacuum distillation column into the second vacuum distillation column has the following composition:
IPDA 90-100 wt %
High boilers 0-10 wt %
Residual ammonia 10-500 ppm,
and
in that the second vacuum distillation column K II has the following parameters:
Pressure 10-200 mbar
Tops temperature 80-200° C.
Theoretical plates 5-50
and
in that the partial condenser used at the top of the second vacuum distillation column K II has the following parameters:
Pressure 10-200 mbar
Temperature 80-200° C.

14. The process according to claim 2, wherein the purity of the pure isophoronediamine is at least 98% by weight and the residual ammonia content in the pure IPDA is less than 50 ppm.

15. The process according to claim 3, wherein the composition of the feed stream crude IPDA II from the first vacuum distillation column into the second vacuum distillation column has the following composition:
IPDA 90-100 wt %
High boilers 0-10 wt %
Residual ammonia 10-500 ppm.

16. The process according to claim 3, wherein the second vacuum distillation column K II has the following parameters:
Pressure 10-200 mbar
Tops temperature 80-200° C.
Theoretical plates 5-50.

17. The process according to claim 3, wherein the partial condenser used at the top of the second vacuum distillation column K II has the following parameters:
Pressure 10-200 mbar
Temperature 80-200° C.

18. The process according to claim 3, wherein the crude isophoronediamine I has the following composition:
IPDA 75-100 wt %
Water 0-15 wt %
Low boilers 0-6 wt %
High boilers 0-6 wt %
Residual ammonia 10-1000 ppm,
and
in that the first vacuum distillation column K I has the following parameters:
Temperature 40-120° C.
Pressure 10-200 mbar Theoretical plates 10-80
and
in that the composition of the feed stream crude IPDA II from the first vacuum distillation column into the second vacuum distillation column has the following composition:
IPDA 90-100 wt %
High boilers 0-10 wt %
Residual ammonia 10-500 ppm, and
in that the second vacuum distillation column K II has the following parameters:
Pressure 10-200 mbar
Tops temperature 80-200° C.
Theoretical plates 5-50
and
in that the partial condenser used at the top of the second vacuum distillation column K II has the following parameters:
Pressure 10-200 mbar
Temperature 80-200° C.

19. The process according to claim 3, wherein the purity of the pure isophoronediamine is at least 98% by weight and the residual ammonia content in the pure IPDA is less than 50 ppm.

20. The process according to claim 4, wherein the second vacuum distillation column K II has the following parameters:
Pressure 10-200 mbar
Tops temperature 80-200° C.
Theoretical plates 5-50.

* * * * *